(12) United States Patent
Lee et al.

(10) Patent No.: US 11,911,152 B2
(45) Date of Patent: Feb. 27, 2024

(54) APPARATUS AND METHOD FOR ESTIMATING CONCENTRATION OF ANALYTE, AND CALIBRATION METHOD

(71) Applicant: SAMSUNG ELECTRONICS CO., LTD., Suwon-si (KR)

(72) Inventors: Jun Ho Lee, Incheon (KR); Sang Kyu Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 904 days.

(21) Appl. No.: 16/836,163

(22) Filed: Mar. 31, 2020

(65) Prior Publication Data

US 2021/0121102 A1    Apr. 29, 2021

(30) Foreign Application Priority Data

Oct. 29, 2019    (KR) .................. 10-2019-0135616

(51) Int. Cl.
| | | |
|---|---|---|
| *A61B 5/1455* | (2006.01) | |
| *A61B 5/145* | (2006.01) | |
| *A61B 5/00* | (2006.01) | |
| *G01J 3/02* | (2006.01) | |
| *G01J 3/42* | (2006.01) | |

(52) U.S. Cl.
CPC ........ *A61B 5/1455* (2013.01); *A61B 5/14532* (2013.01); *A61B 5/7275* (2013.01); *G01J 3/0202* (2013.01); *G01J 3/0297* (2013.01); *G01J 3/42* (2013.01); *A61B 2560/0233* (2013.01)

(58) Field of Classification Search
CPC .................................................. A61B 5/1455
See application file for complete search history.

(56) References Cited

U.S. PATENT DOCUMENTS

| | | |
|---|---|---|
| 6,635,491 B1 | 10/2003 | Khalil et al. |
| 7,248,911 B2 | 7/2007 | Jeon et al. |

(Continued)

FOREIGN PATENT DOCUMENTS

| | | |
|---|---|---|
| CN | 105352898 B | 1/2018 |
| EP | 1 459 679 A1 | 9/2004 |

(Continued)

OTHER PUBLICATIONS

Communication dated Oct. 16, 2020 issued by the European Intellectual Property Office in counterpart European Application No. 20191027.0.

(Continued)

*Primary Examiner* — Marjan Fardanesh
(74) *Attorney, Agent, or Firm* — Sughrue Mion, PLLC

(57) ABSTRACT

An apparatus for estimating a concentration of an analyte includes an optical sensor configured to emit light toward an object and receive light reflected from the object; and a processor configured to obtain a ratio of an absorption coefficient to a scattering coefficient based on the received light, obtain a first absorption spectrum of the object based on the obtained ratio, obtain a second absorption spectrum by eliminating a scattering correction spectrum from the first absorption spectrum, the scattering correction spectrum corresponding to a nonlinear change in the scattering coefficient according to a wavelength of the emitted light, and estimate a concentration of an analyte based on the second absorption spectrum.

25 Claims, 10 Drawing Sheets

(56) References Cited

U.S. PATENT DOCUMENTS

| | | |
|---|---|---|
| 7,616,303 B2 | 11/2009 | Yang et al. |
| 7,640,140 B2 | 12/2009 | Ruchti et al. |
| 8,873,035 B2 | 10/2014 | Yang et al. |
| 10,004,399 B2 | 6/2018 | Anikanov et al. |
| 10,073,032 B2 | 9/2018 | Choung |
| 10,258,236 B2 | 4/2019 | Anikanov et al. |
| 10,582,855 B2 | 3/2020 | Anikanov et al. |
| 2007/0179367 A1 | 8/2007 | Ruchti et al. |
| 2010/0123897 A1 | 5/2010 | Yang et al. |
| 2013/0012794 A1 | 1/2013 | Zeng et al. |
| 2015/0131098 A1 | 5/2015 | Yang et al. |
| 2015/0305681 A1 | 10/2015 | Nadkarni |
| 2016/0278715 A1 | 9/2016 | Yu et al. |
| 2016/0361004 A1 | 12/2016 | Lange et al. |
| 2017/0223316 A1 | 8/2017 | Zeng et al. |
| 2018/0041675 A1 | 2/2018 | Cheng et al. |
| 2018/0275049 A1 | 9/2018 | Mazzotti et al. |

FOREIGN PATENT DOCUMENTS

| | | |
|---|---|---|
| EP | 3 505 052 A1 | 7/2019 |
| JP | 2015-040744 A | 3/2015 |
| KR | 10-2015-0112902 A | 10/2015 |
| KR | 10-2018-0059355 A | 6/2018 |
| WO | 2008152604 A1 | 12/2008 |
| WO | 2009004541 A1 | 1/2009 |
| WO | 2014/100378 A1 | 6/2014 |
| WO | 2015147403 A1 | 10/2015 |

OTHER PUBLICATIONS

Luigi Rovati et al., "Design and performance of a wide-bandwidth and sensitive instrument for near-infrared spectroscopic measurements on human tissue", Review of Scientific Instruments, vol. 75, No. 12, ISSN: 0034-6748, DOI: 10.1063/1.1818588, Nov. 30, 2004, pp. 5315-5325, 11 pages total, XP012071967.

APPARATUS AND METHOD FOR ESTIMATING CONCENTRATION OF ANALYTE, AND CALIBRATION METHOD

CROSS-REFERENCE TO RELATED APPLICATION(S)

This application claims priority from Korean Patent Application No. 10-2019-0135616, filed on Oct. 29, 2019, in the Korean Intellectual Property Office, the entire disclosure of which is incorporated herein by reference for all purposes.

BACKGROUND

1. Field

Example embodiments consistent with the disclosure relate to an apparatus and a method for estimating the concentration of an in vivo analyte.

2. Description of the Related Art

Diabetes is a chronic disease that may cause various complications and can be difficult to cure, and hence patients with diabetes are advised to check their blood glucose regularly to prevent complications. In particular, when insulin is administered to control a blood glucose level, the blood glucose level should be closely monitored to avoid hypoglycemia and control an insulin dosage. An invasive method of finger pricking is generally used to measure blood glucose levels. However, while the invasive method may provide high reliability in measurement, it may cause pain and inconvenience as well as an increased risk of infections due to the injection to collect blood. Recently, research has been conducted on methods of non-invasively measuring a blood glucose level by using a spectrometer without blood sampling.

However, in the case of a turbid medium such as skin, it is difficult to accurately estimate an analyte concentration due to a change in a length of an optical path (or a light path length) caused by a change in a scattering coefficient. Accordingly, there is a need for technology for accurate estimation of the analyte concentration even in a turbid medium.

SUMMARY

One or more example embodiments of the disclosure provide an apparatus and a method for estimating the concentration of an in vivo analyte with improved accuracy, and a calibration method thereof.

According to an aspect of an example embodiment, there is provided an apparatus for estimating a concentration of an analyte, the apparatus including: an optical sensor configured to emit light toward an object and receive light reflected from the object; and a processor configured to obtain a ratio of an absorption coefficient to a scattering coefficient based on the received light, obtain a first absorption spectrum of the object based on the obtained ratio, obtain a second absorption spectrum by eliminating a scattering correction spectrum from the first absorption spectrum, the scattering correction spectrum corresponding to a nonlinear change in the scattering coefficient according to a wavelength of the emitted light, and estimate a concentration of an analyte based on the second absorption spectrum.

The processor may be further configured to obtain a reflectance of the object based on the received light, obtain an albedo of the object based on the obtained reflectance, and obtain the ratio of the absorption coefficient to the scattering coefficient based on the obtained albedo.

The processor may be further configured to obtain the first absorption spectrum based on a function of the ratio of the absorption coefficient to the scattering coefficient.

The scattering correction spectrum may be expressed as a function representing a change in a length of a light path according to the wavelength of the emitted light; and the processor may be further configured to obtain the second absorption spectrum by using a scattering correction model that is based on the function.

The processor may be further configured to generate a plurality of candidate scattering correction models by varying coefficients of the function, obtain a plurality of second absorption spectra by using the first absorption spectrum and the plurality of candidate scattering correction models, estimate a concentration of an analyte for each of the plurality of second absorption spectra, and select, as the scattering correction model, a candidate scattering correction model, in which a difference between an estimated concentration and an actual concentration of the analyte is minimum, from among the plurality of candidate scattering correction models.

The processor may be further configured to estimate the concentration of the analyte by using the second absorption spectrum and a pure component spectrum of the analyte.

The pure component spectrum of the analyte may be set as a default or may be obtained and set in a calibration mode.

In the calibration mode, the processor may be further configured to obtain the pure component spectrum based on a difference between the second absorption spectrum, obtained when the concentration of the analyte in the object is a first concentration, and the second absorption spectrum obtained when the concentration of the analyte in the object is a second concentration.

The processor may be further configured to obtain the second absorption spectrum by eliminating the scattering correction spectrum from the first absorption spectrum by using one of Principal Component Analysis (PCA), Independent Component Analysis (ICA), Non-negative Matrix Factorization (NMF), and Singular Value Decomposition (SVD).

The analyte may include at least one of glucose, triglyceride, urea, uric acid, lactate protein, cholesterol, antioxidant substance, and ethanol.

According to an aspect of an example embodiment, there is provided a method of estimating a concentration of an analyte, the method including: emitting light toward an object and receiving light reflected from the object; obtaining a ratio of an absorption coefficient to a scattering coefficient based on the received light; obtaining a first absorption spectrum of the object from the obtained ratio of the absorption coefficient to the scattering coefficient; obtaining a second absorption spectrum by eliminating a scattering correction spectrum from the first absorption spectrum, the scattering correction spectrum corresponding to a nonlinear change in the scattering coefficient according to a wavelength of the emitted light; and estimating a concentration of an analyte based on the second absorption spectrum.

The obtaining the ratio may include obtaining reflectance of the object based on the received light; obtaining an albedo of the object based on the obtained reflectance; and obtaining the ratio of the absorption coefficient to the scattering coefficient based on the obtained albedo.

The obtaining the first absorption spectrum may include obtaining the first absorption spectrum based on a function of the ratio of the absorption coefficient to the scattering coefficient.

The scattering correction spectrum may be expressed as a function representing a change in a length of a light path according to the wavelength of the emitted light; and the obtaining the second absorption spectrum may include obtaining the second absorption spectrum by using a scattering correction model based on the function.

The estimating may include estimating the concentration of the analyte by using the second absorption spectrum and a pure component spectrum of the analyte.

The pure component spectrum of the analyte may be set as a default or may be obtained and set in a calibration mode.

The obtaining the second absorption spectrum may include obtaining the second absorption spectrum by eliminating the scattering correction spectrum from the first absorption spectrum by using one of Principal Component Analysis (PCA), Independent Component Analysis (ICA), Non-negative Matrix Factorization (NMF), and Singular Value Decomposition (SVD).

The analyte may include at least one of glucose, triglyceride, urea, uric acid, lactate, protein, cholesterol, antioxidant substance, and ethanol.

According to an aspect of an example embodiment, there is provided a method of calibrating an apparatus for estimating a concentration of an analyte, the calibration method including: emitting light toward an object and receiving light reflected from the object; obtaining a ratio of an absorption coefficient to a scattering coefficient based on the received light; obtaining a first absorption spectrum of the object from the obtained ratio of the absorption coefficient to the scattering coefficient; generating a plurality of candidate scattering correction models by varying coefficients of a function representing a change in a length of a light path according to a wavelength of the emitted light; obtaining a plurality of second absorption spectra by using the first absorption spectrum and the plurality of candidate scattering correction models; estimating a concentration of an analyte for each of the plurality of second absorption spectra; and selecting a candidate scattering correction model, in which a difference between an estimated concentration and an actual concentration of the analyte is minimum, from among the plurality of candidate scattering correction models.

The obtaining the ratio may include obtaining reflectance of the object based on the received light; obtaining an albedo of the object based on the obtained reflectance; and obtaining the ratio of the absorption coefficient to the scattering coefficient based on the obtained albedo.

The obtaining the first absorption spectrum may include obtaining the first absorption spectrum based on a function of the ratio of the absorption coefficient to the scattering coefficient.

The estimating may include estimating the concentration of the analyte for each of the plurality of second absorption spectra by using each of the plurality of second absorption spectra and a pure component spectrum of the analyte.

The obtaining the plurality of second absorption spectra may include obtaining the plurality of second absorption spectra by using one of Principal Component Analysis (PCA), Independent Component Analysis (ICA), Non-negative Matrix Factorization (NMF), and Singular Value Decomposition (SVD).

The analyte may include at least one of glucose, triglyceride, urea, uric acid, lactate, protein, cholesterol, antioxidant substance, and ethanol.

According to an aspect of an example embodiment, there is provided a method of calibrating an apparatus for estimating a concentration of an analyte, the method including: emitting first light toward an object and receiving second light reflected from the object, a concentration of an analyte in the object being a first concentration; obtaining a first ratio of an absorption coefficient to a scattering coefficient based on the received second light; obtaining a first absorption spectrum of the object from the obtained first ratio; obtaining a second absorption spectrum by eliminating a first scattering correction spectrum from the first absorption spectrum, the scattering correction spectrum corresponding to a nonlinear change in the scattering coefficient according to a wavelength of the emitted first light; emitting third light toward the object and receiving fourth light reflected from the object, the concentration of the analyte in the object being a second concentration; obtaining a second ratio of the absorption coefficient to the scattering coefficient based on the received fourth light; obtaining a third absorption spectrum of the object from the obtained second ratio; obtaining a fourth absorption spectrum of the analyte by eliminating a second scattering correction spectrum from the third absorption spectrum, the second scattering correction spectrum corresponding to the nonlinear change in the scattering coefficient according to a wavelength of the emitted third light; and obtaining a pure component spectrum of the analyte based on the obtained second absorption spectrum and the obtained fourth absorption spectrum.

The obtaining the pure component spectrum may include obtaining the pure component spectrum by using a difference between the fourth absorption spectrum and the second absorption spectrum, and a difference between the second concentration and the first concentration.

The method may further include generating a concentration estimation model by using the obtained pure component spectrum.

BRIEF DESCRIPTION OF THE DRAWINGS

The above and/or other aspects and features of certain example embodiments will be more apparent from the following description taken in conjunction with the accompanying drawings, in which.

DETAILED DESCRIPTION

Figure 1:
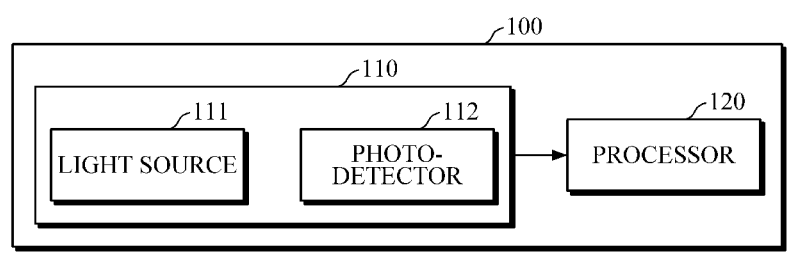
FIG. 1 is a block diagram illustrating an apparatus for estimating a concentration of an analyte according to an example embodiment.

Hereinafter, example embodiments of the disclosure will be described in detail with reference to the accompanying drawings. It should be noted that wherever possible, the same reference symbols refer to same parts even in different drawings. In the following description, a detailed description of known functions and configurations incorporated herein will be omitted when it may obscure the subject matter of the disclosure.

Throughout the drawings and the detailed description, unless otherwise described, the same drawing reference numerals will be understood to refer to the same elements, features, and structures. The relative size and depiction of these elements may be exaggerated for clarity, illustration, and convenience.

Process steps described herein may be performed differently from a specified order, unless a specified order is clearly stated as being necessary in the context of the disclosure. That is, each step may be performed in a specified order, at substantially the same time, or in a reverse order, or in any order that is different from the specified order.

Further, the terms used throughout this specification are defined in consideration of the functions according to example embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Further, components that will be described in the specification are discriminated merely according to functions mainly performed by the components. That is, two or more components which will be described later can be integrated into a single component. Furthermore, a single component can be separated into two or more components. Moreover, each component which will be described can additionally perform some or all of a function executed by another component in addition to the main function thereof. Some or all of the main function of each component can be carried out by another component. Each component may be implemented as hardware, software, or a combination of both.

FIG. 1 is a block diagram illustrating an apparatus for estimating a concentration of an analyte according to an example embodiment.

An apparatus 100 for estimating an analyte concentration of FIG. 1 may measure a concentration of an in vivo analyte by analyzing an absorption spectrum of an object, and may be included in an electronic device or may be enclosed in a housing to be provided as a separate device. Examples of the electronic device may include a cellular phone, a smartphone, a tablet personal computer (PC), a laptop computer, a personal digital assistant (PDA), a portable multimedia player (PMP), a navigation device, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited to the above examples.

Here, the analyte may include glucose, triglyceride, urea, uric acid, lactate, protein, cholesterol, antioxidant substances (e.g., vitamin, carotenoid, flavonoid, ascorbic acid, tocopherol, etc.), ethanol, and the like but is not limited thereto. In the case where the in vivo analyte is glucose, the analyte concentration may indicate a blood glucose level.

Referring to FIG. 1, the apparatus 100 for estimating an analyte concentration may include an optical sensor 110 and a processor 120.

The optical sensor 110 may emit light toward an object, and may receive light reflected from the object. The optical sensor 110 includes a light source 111 and a photodetector 112.

The light source 111 may emit light toward the object. For example, the light source 111 may emit light of a predetermined wavelength, e.g., visible light or infrared light, toward the object. However, wavelengths of light emitted by the light source 111 may vary depending on the measurement purpose or types of concentrations. Further, the light source 111 may not be a single light source, and may include an array of a plurality of light sources. In the case where the light source 111 includes a plurality of light sources, the plurality of light sources may emit light of the same wavelength or light of different wavelengths. Further, the plurality of light sources may be classified into a plurality of groups, and each group of the light-sources may emit light of different wavelengths.

In one example embodiment, the light source 111 may be formed as a light emitting diode (LED), a laser diode, a phosphor, and the like.

Further, the light source 111 may further include an optical element (e.g., filter, reflecting mirror, etc.) for selecting light of a desired wavelength or for directing light emitted by the light source 111 toward a desired position.

The photodetector 112 may receive light reflected from the object. The photodetector 112 may not be a single device, and may include an array of a plurality of devices.

In one example embodiment, the photodetector 112 may include a photo diode, a photo transistor, an image sensor (e.g., a charge-coupled device (CCD) a complementary metal-oxide semiconductor (CMOS), etc.), or the like, but is not limited thereto.

Further, the photodetector 112 may further include an optical element (e.g., filter, reflecting mirror, etc.) for selecting light of a desired wavelength or for directing light reflected from the object toward the photodetector 112.

The processor 120 may process various signals and operations related to generating a scattering correction model, obtaining a pure component spectrum, obtaining and correcting an absorption spectrum, generating a concentration estimation model, estimating a concentration, and the like. The processor 120 may include a micro-processor or a central processing unit (CPU).

The processor 120 may operate in a calibration mode or in a concentration estimation mode. Here, the calibration mode may be a mode for building a model for use in estimating a concentration, and the concentration estimation mode may be a mode for estimating a concentration by using the model built in the calibration mode.

Hereinafter, the calibration mode and the concentration estimation mode will be described.

<Calibration Mode>

In the calibration mode according to an example embodiment, the processor 120 may generate a scattering correction model, for use in eliminating the effect of a nonlinear change in a scattering coefficient from an absorption spectrum, and generate a concentration estimation model for use in estimating the concentration of an analyte.

(1) Generating a Scattering Correction Model

The processor 120 may control the optical sensor 110 to emit light toward an object and to receive light reflected from the object.

The processor 120 may obtain a ratio of an absorption coefficient to a scattering coefficient based on the received light. For example, the processor 120 may obtain reflectance of the object by using a quantity of the received light, and may obtain an albedo of the object by using the following Equation 1. Further, the processor 120 may obtain a ratio of the absorption coefficient to the scattering coefficient by using the following Equation 2.

$$R = \frac{a'}{1 + 2k(1-a') + \left(1 + \frac{2k}{3}\right)\sqrt{3(1-a')}}$$ [Equation 1]

$$k = \frac{1 + r_d}{1 - r_d}$$

$$r_d = -1.440 n_{rel}^{-2} + 0.710 n_{rel}^{-1} + 0.668 + 0.0636 n_{rel}$$

Herein, R denotes the reflectance, a' denotes the albedo, and $n_{rel}$ denotes a ratio ($n_{rel} = n_{medium}/n_{air}$, where $n_{air}=1$) of a refractive index of a medium to a refractive index of air.

$$\frac{\mu_a}{\mu'_s} = \frac{1}{a'} - 1$$ [Equation 2]

Herein, $\mu_a$ denotes the absorption coefficient, and $\mu'_s$ denotes the scattering coefficient.

Upon obtaining the ratio of the absorption coefficient to the scattering coefficient, the processor 120 may obtain a first absorption spectrum of the object from the obtained ratio of the absorption coefficient to the scattering coefficient.

Absorbance of the object may be represented by the following Equation 3, and a light path length may be represented by the following Equation 4.

$$\text{Absorbance} = \mu_a * l$$ [Equation 3]

$$l = \frac{1}{\sqrt{3\mu_a \times (\mu'_s + \mu_a)}}$$ [Equation 4]

Herein, l denotes the light path length.

By substituting the expression of the light path length in Equation 4 into Equation 3, the absorbance of the object may be expressed as a function of the ratio of the absorption coefficient to the scattering coefficient, as represented by the following Equation 5.

$$\text{Absorbance} = f\left(\frac{\mu_a}{\mu'_s}\right) = \frac{\sqrt{\frac{\mu_a}{\mu'_s}}}{\sqrt{3\left(1 + \frac{\mu_a}{\mu'_s}\right)}}$$ [Equation 5]

In one example embodiment, the processor 120 may calculate absorbance of the object by using Equation 5, and may obtain the first absorption spectrum based on the calculated absorbance. As discussed above, the absorbance of the object may be expressed as the function of the ratio of the absorption coefficient to the scattering coefficient, as represented by Equation 5.

The scattering coefficient may have a monotonic characteristic, in which the scattering coefficient decreases with an increasing wavelength. Accordingly, such a monotonic characteristic of the scattering coefficient may be expressed as a monotonic function by the following Equation 6.

$$\mu'_s(\lambda) = A\lambda^{-B}$$ [Equation 6]

Herein, $\lambda$ denotes a wavelength; $\mu'_s(\lambda)$ denotes a scattering coefficient at the wavelength of $\lambda$; and A and B denote coefficients related to scatter density and Mie scatter size, respectively.

By substituting the expression of the scattering coefficient in Equation 6 into Equation 4 for approximation, the light path length may be approximated by the following Equation 7.

$$l = \frac{1}{\sqrt{3\mu_a \times (\mu'_s + \mu_a)}} \sim \frac{1}{C\sqrt{(1 + D\lambda^{-B})}} \sim E + F\lambda^m$$ [Equation 7]

As represented by Equation 7, the light path length may be expressed as a nonlinear function with respect to a wavelength of the light.

A change in the scattering coefficient causes a change in the light path length, such that by correcting the effect of a linear change in the light path length according to a wavelength, the effect of a nonlinear change in the scattering coefficient according to the wavelength may be corrected.

That is, by using Equation 7, which represents the nonlinear change in the light path length according to the wavelength, the processor 120 may generate a scattering correction model as represented by the following Equation 8.

$$S_{raw} = k \times (E + F\lambda^m) + S_{corr}$$ [Equation 8]

Herein, $S_{raw}$ denotes a first absorption spectrum, $S_{corr}$ denotes a second absorption spectrum obtained by correction, $(E + F\lambda^m)$ denotes a scattering correction spectrum, which indicates the effect of the nonlinear change in the scattering coefficient according to the wavelength or the effect of the nonlinear change in the light path length according to the wavelength, k denotes a contribution of the scattering correction spectrum, and E, F, and m denote coefficients.

Here, k may be obtained, along with the second absorption spectrum, in a process in which the second absorption spectrum is obtained by eliminating the effect of the scattering correction spectrum from the first absorption spectrum by using various dimension reduction algorithms, such as Principal Component Analysis (PCA), Independent Component Analysis (ICA), Non-negative Matrix Factorization (NMF), Singular Value Decomposition (SVD), and the like.

In addition, E, F, and m may be determined by the following method.

The processor 120 may generate a plurality of candidate scattering correction models by varying the coefficients E, F, and m. Further, by using the generated plurality of candidate scattering correction models, the processor 120 may obtain a plurality of second absorption spectra. By using a default concentration estimation model which is represented by the following Equation 9, the processor 120 may estimate an analyte concentration for each of the second absorption spectra.

$$S_{corr} = \varepsilon_g C_g + \varepsilon_1 C_1 + \varepsilon_2 C_2 + \ldots \quad \text{[Equation 9]}$$

Herein, $\varepsilon_g$ denotes a pure component spectrum of an analyte which is set as a default, $C_g$ denotes the concentration of the analyte, $\varepsilon_1$ and $\varepsilon_2$ respectively denote pure component spectra of substances other than the analyte set as the default, and $C_1$ and $C_2$ respectively denote concentrations of substances other than the analyte.

Further, the processor 120 may determine E, F, and m by selecting a candidate scattering correction model which is used for obtaining a second absorption spectrum, at which a difference between an estimated concentration and an actual concentration is minimum, from among the plurality of candidate scattering correction models.

(2) Generating a Concentration Estimation Model

In the case where the concentration of an analyte in an object is a first concentration, the processor 120 may control the optical sensor 110 to emit light toward the object and to receive light reflected from the object.

The processor 120 may obtain a ratio of the absorption spectrum to the scattering coefficient based on the received light. For example, the processor 120 may obtain reflectance of the object by using a quantity of the received light, and may obtain an albedo of the object by using Equation 1 based on the obtained reflectance. Further, the processor 120 may obtain a ratio of the absorption coefficient to the scattering coefficient by using Equation 2 based on the obtained albedo.

Upon obtaining the ratio of the absorption coefficient to the scattering coefficient, the processor 120 may obtain a first absorption spectrum of the object from the obtained ratio of the absorption coefficient to the scattering coefficient.

By eliminating the scattering correction spectrum, which indicates the effect of the nonlinear change in the scattering coefficient according to a wavelength, from the first absorption spectrum by using the scattering correction model represented by Equation 8, the processor 120 may obtain the second absorption spectrum when the concentration of the analyte is the first concentration.

By using the method described above, the processor 120 may obtain the second absorption spectrum when the concentration of the analyte is a second concentration. In this case, the second concentration may be a different value from the first concentration.

The processor 120 may obtain a pure component spectrum of the analyte based on the second absorption spectrum when the analyte concentration is the first concentration and the second absorption spectrum when the analyte concentration is the second concentration. For example, the processor 120 may obtain the pure component spectrum of the analyte by using the following Equation 10.

$$\varepsilon'_g = \frac{S_{corr2} - S_{corr1}}{C_{g2} - C_{g1}} \quad \text{[Equation 10]}$$

Herein, $\varepsilon'_g$ denotes the pure component spectrum of the analyte, $C_{g1}$ and $C_{g2}$ denote the first concentration and the second concentration, respectively, and $S_{corr1}$ and $S_{corr2}$ denote the second absorption spectrum obtained at the first concentration and the second absorption spectrum obtained at the second concentration, respectively.

Upon obtaining the pure component spectrum of the analyte, the processor 120 may generate a concentration estimation model as represented by the following Equation 11.

$$S_{corr} = \varepsilon'_g C_g + \varepsilon_1 C_1 + \varepsilon_2 C_2 + \ldots \quad \text{[Equation 11]}$$

<Concentration Estimation Mode>

In the concentration estimation mode according to an example embodiment, the processor 120 may control the optical sensor 110 to emit light toward the object and to receive light reflected from the object.

The processor 120 may obtain a ratio of the absorption coefficient to the scattering coefficient based on the received light. For example, the processor 120 may obtain reflectance of the object by using a quantity of the received light, and may obtain an albedo of the object by using Equation 1 based on the obtained reflectance. Further, the processor 120 may obtain a ratio of the absorption coefficient to the scattering coefficient by using Equation 2 based on the obtained albedo.

Upon obtaining the ratio of the absorption coefficient to the scattering coefficient, the processor 120 may obtain a first absorption spectrum of the object from the obtained ratio of the absorption coefficient to the scattering coefficient.

By eliminating the scattering correction spectrum, which indicates the effect of the nonlinear change in the scattering coefficient according to a wavelength, from the first absorption spectrum by using the scattering correction model represented by Equation 8, the processor 120 may obtain a second absorption spectrum.

Upon obtaining the second absorption spectrum, the processor 120 may estimate the analyte concentration by using the concentration estimation model of Equation 9 or Equation 11. In this case, the processor 120 may estimate the analyte concentration by using various dimension reduction algorithms, such as Principal Component Analysis (PCA), Independent Component Analysis (ICA), Non-negative Matrix Factorization (NMF), Singular Value Decomposition (SVD), and the like.

Figure 2:
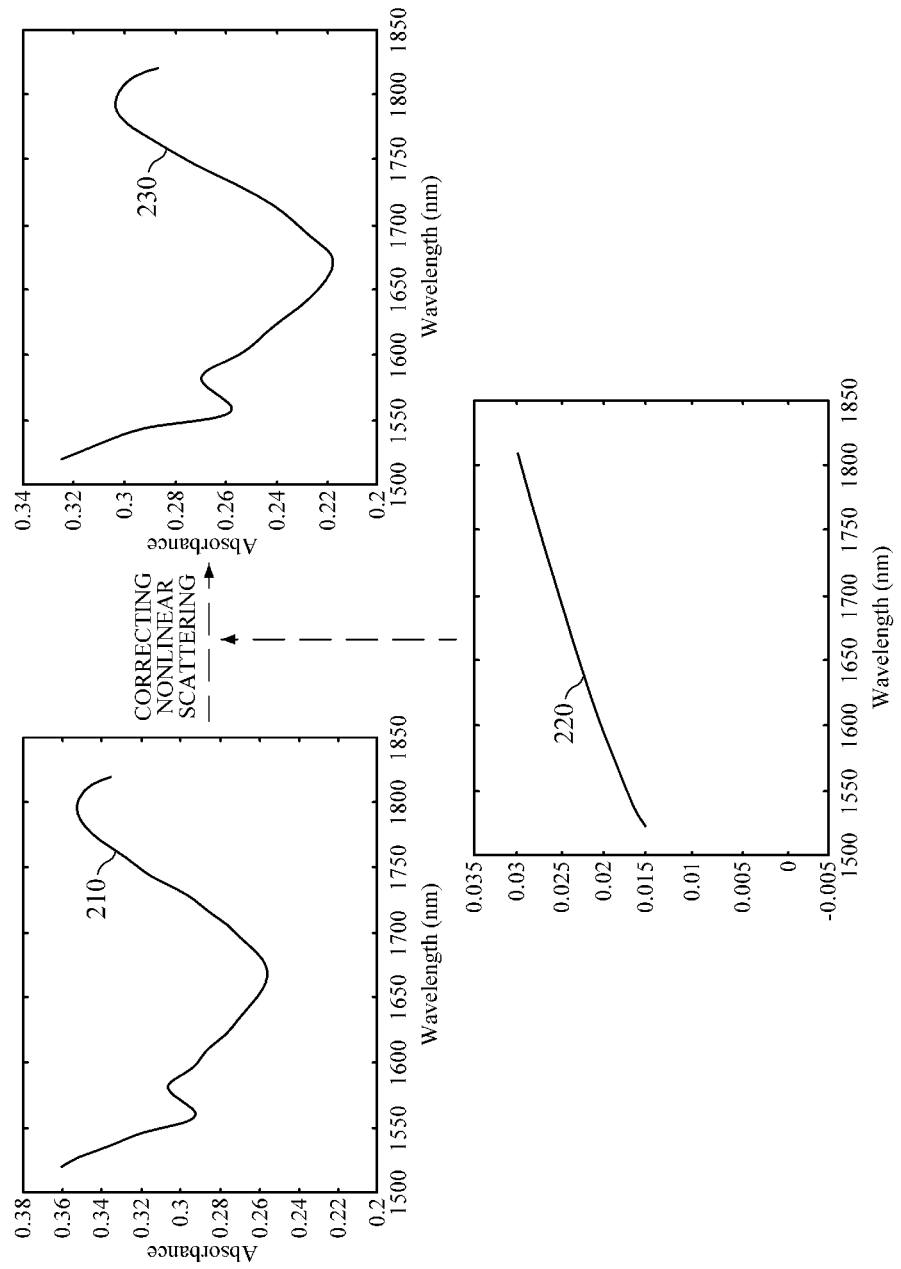
FIG. 2 is a diagram explaining a method of correcting an effect of a nonlinear change in a scattering coefficient with wavelength according to an example embodiment.

FIG. 2 is a diagram explaining a method of correcting an effect of a nonlinear change in scattering coefficient according to a wavelength according to an example embodiment.

Referring to FIGS. 1 and 2, by controlling the optical sensor 110 to receive light, the processor 120 may obtain reflectance of an object by using a quantity of the received light, and may obtain a ratio of an absorption coefficient to a scattering coefficient based on the obtained reflectance by using Equations 1 and 2.

Upon obtaining the ratio of the absorption coefficient to the scattering coefficient, the processor 120 may obtain a first absorption spectrum 210 of the object from the obtained ratio of the absorption coefficient to the scattering coefficient by using Equation 5.

The processor may generate a second absorption spectrum 230 by eliminating a scattering correction spectrum 220, which indicates the effect of a nonlinear change in the scattering coefficient according to a wavelength or the effect of the nonlinear change in the light path length according to a wavelength, from the first absorption spectrum 210 by using the scattering correction model of Equation 8 which is generated in the calibration mode.

Figure 3:
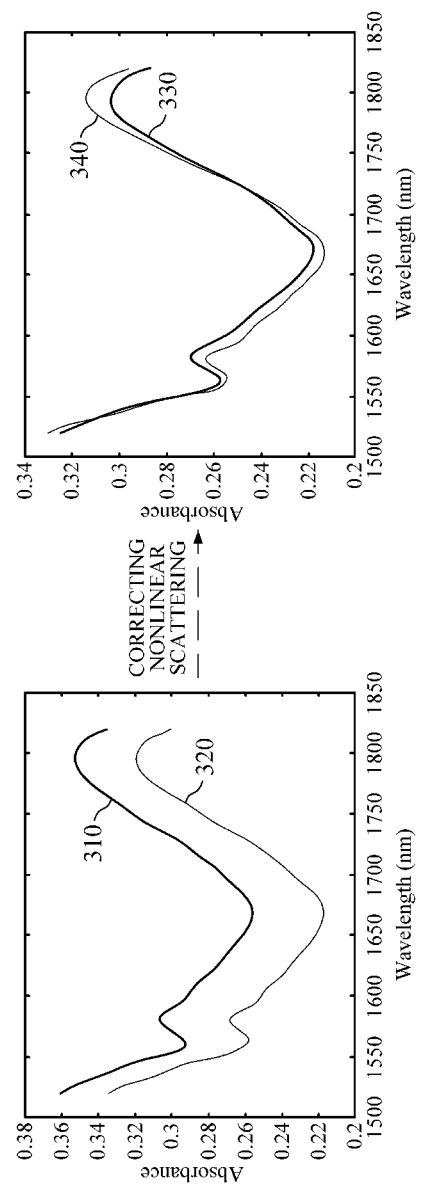
FIG. 3 is a diagram explaining a difference in second absorption spectra at each concentration according to an example embodiment.

FIG. 3 is a diagram explaining a difference in second absorption spectra at each concentration according to an example embodiment.

In the example of FIG. 3, reference numeral 310 denotes a first absorption spectrum when an analyte concentration is $10^4$ mg/dl, and reference numeral 320 denotes a first absorption spectrum when an analyte concentration is $10^3$ mg/dl.

A second absorption spectrum 330 may be obtained by correcting the effect of a nonlinear change in scattering coefficient according to a wavelength in the first absorption spectrum 310 when the analyte concentration is $10^4$ mg/dl. Further, a second absorption spectrum 340 may be obtained by correcting the effect of a nonlinear change in scattering coefficient according to a wavelength in the first absorption spectrum 320 when the analyte concentration is $10^3$ mg/dl.

As illustrated in FIG. 3, before correction, the reduced scattering coefficient due to the analyte causes a change in a light path length, such that an offset may occur between absorption spectra at each concentration of the analyte. By contrast, after correction, the offset between the absorption spectra at each concentration of the analyte is reduced.

Figure 4:
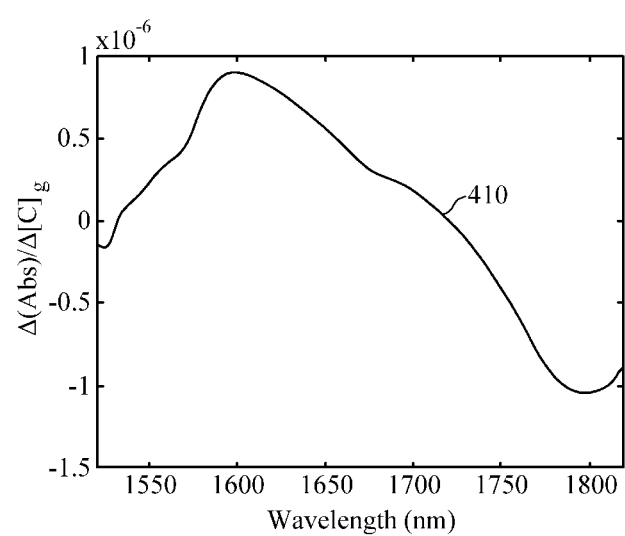
FIG. 4 is a diagram illustrating obtaining a pure component spectrum of an analyte according to an example embodiment.

FIG. 4 is a diagram illustrating obtaining a pure component spectrum of an analyte according to an example embodiment.

Referring to FIGS. 1, 3, and 4, the processor 120 may obtain a pure component spectrum of an analyte by using Equation 10. For example, based on the second absorption spectrum 330 when the analyte concentration is $10^4$ mg/dl, and the second absorption spectrum 340 when the analyte concentration is $10^3$ mg/dl, the processor 120 may obtain a pure component spectrum 410 of the analyte by using Equation 10.

Figure 5:
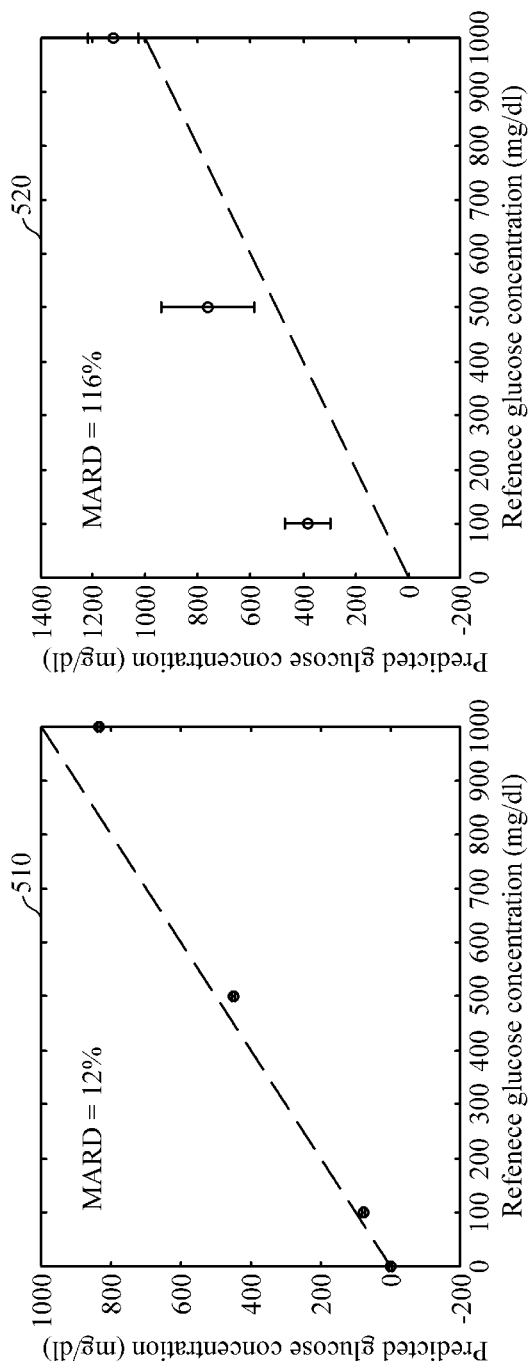
FIG. 5 is a diagram explaining a result of estimating an analyte concentration according to an example embodiment.

FIG. 5 is a diagram explaining a result of estimating an analyte concentration according to an example embodiment.

A graph diagram 510 in FIG. 5 shows a result of estimating an analyte concentration by a method according to an example embodiment, for example, by obtaining a first absorption spectrum by using an absorbance calculation equation (e.g., Equation 5), which is expressed as a function of a ratio of an absorption coefficient to a scattering coefficient, and by obtaining a second absorption spectrum by eliminating an effect of a nonlinear change in the scattering coefficient from the first absorption spectrum. A graph diagram 520 in FIG. 5 shows a result of estimating an analyte concentration by a basic comparative method, for example, by obtaining a first absorption spectrum by using an absorbance calculation equation (absorbance=$\log(1/R)$), which is expressed as a function of a reciprocal of reflectance, and by obtaining a second absorption spectrum by correcting the effect of a linear change in scattering coefficient by using Multiplicative Scattering Correction (MSC).

As illustrated in FIG. 5, a maximum absolute relative difference (MARD) is 116% in the comparative method, but in the method according to an example embodiment of the disclosure, MARD is 12%, showing that linearity of quantitative measurement of the analyte concentration is greatly improved according to an example embodiment.

Figure 6:
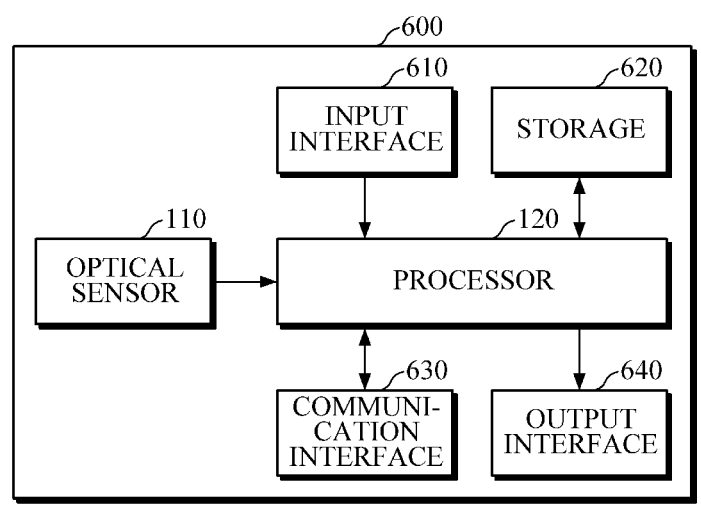
FIG. 6 is a block diagram illustrating an apparatus for estimating a concentration of an analyte according to an example embodiment.

FIG. 6 is a block diagram illustrating an apparatus for estimating a concentration of an analyte according to an example embodiment.

An apparatus 600 for estimating an analyte concentration of FIG. 6 may measure the concentration of an in vivo analyte by analyzing an absorption spectrum of an object, and may be included in an electronic device or may be enclosed in a housing to be provided as a separate device. Examples of the electronic device may include a cellular phone, a smartphone, a tablet PC, a laptop computer, a personal digital assistant (PDA), a portable multimedia player (PMP), a navigation device, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited to the above examples.

Referring to FIG. 6, the apparatus 600 for estimating an analyte concentration includes the optical sensor 110, the processor 120, an input interface 610, a storage 620, a communication interface 630, and an output interface 640. Here, the optical sensor 110 and the processor 120 are substantially the same or similar to those described above with reference to FIGS. 1 to 5, such that detailed description thereof will be omitted.

The input interface 610 may receive input of various operation signals from a user. In one example embodiment, the input interface 610 may include a keypad, a dome switch, a touch pad (e.g., static pressure and/or capacitive type touch pad), a jog wheel, a jog switch, a hardware (H/W) button, or the like. The touch pad, which forms a layer structure with a display, may be called a touch screen.

The storage 620 may store programs or commands for operation of the apparatus 600 for estimating an analyte concentration, and may store data input to and/or output from the apparatus 600 for estimating an analyte concentration. Further, the storage 620 may store data processed by the apparatus 600 for estimating an analyte concentration, data (e.g., various models) for performing data processing of the apparatus 600 for estimating an analyte concentration, and the like.

The storage 620 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the apparatus 600 for estimating an analyte concentration may operate in association with an external storage medium, such as web storage and the like, which performs a storage function of the storage 620 on the Internet.

The communication interface 630 may communicate with an external device. For example, the communication interface 630 may transmit, to the external device, data used by the apparatus 600 for estimating an analyte concentration, processing result data of the apparatus 600 for estimating an analyte concentration, and the like; or may receive, from the external device, various data useful for generating a model and/or estimating an analyte concentration.

In this case, the external device may be medical equipment that employs the data used by the apparatus 600 for estimating an analyte concentration, the processing result data of the apparatus 600 for estimating an analyte concentration, and the like, a printer to print out results, or a display to display the results. In addition, the external device may be a digital television (TV), a desktop computer, a cellular phone, a smartphone, a tablet PC, a laptop computer, a personal digital assistant (PDA), a portable multimedia player (PMP), a navigation device, an MP3 player, a digital camera, a wearable device, or the like, but the external device is not limited thereto.

The communication interface 630 may communicate with the external device by using one or more of Bluetooth communication, Bluetooth Low Energy (BLE) communication, Near Field Communication (NFC), wireless local area network (WLAN) communication, Zigbee communication, Infrared Data Association (IrDA) communication, Wireless Fidelity (Wi-Fi) Direct (WFD) communication, Ultra-Wideband (UWB) communication, Ant+ communication, WI-FI communication, Radio Frequency Identification (RFID) communication, third generation (3G) communication, fourth generation (4G) communication, fifth generation (5G) communication, and the like. However, these are merely examples and not intended to be limiting.

The output interface 640 may output the data used by the apparatus 600 for estimating an analyte concentration, the processing result data of the apparatus 600 for estimating an analyte concentration, and the like. In one example embodiment, the output interface 640 may output the data used by the apparatus 600 for estimating an analyte concentration, the processing result data of the apparatus 600 for estimating an analyte concentration, and the like by using at least one of an acoustic method, a visual method, and a tactile method. To this end, the output interface 640 may include a display, a speaker, a vibrator, and the like.

Figure 7:
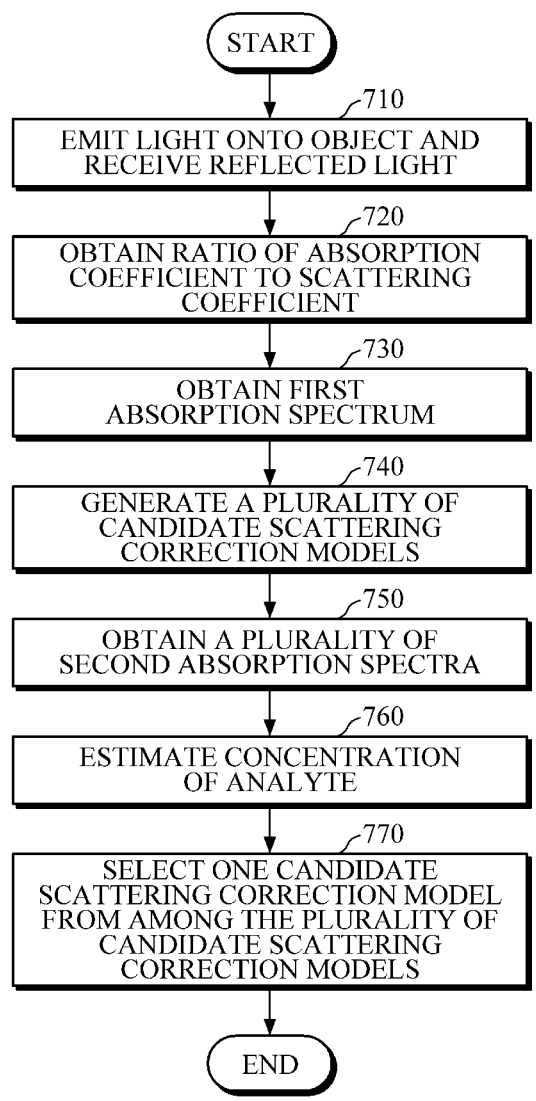
FIG. 7 is a flowchart illustrating a method for generating a scattering correction model according to an example embodiment.

FIG. 7 is a flowchart illustrating a method for generating a scattering correction model according to an example embodiment. The method of generating a scattering correction model of FIG. 7 may be performed by any one of the apparatus 100 of FIG. 1 and apparatus 600 of FIG. 6.

Referring to FIG. 7, the apparatus for estimating an analyte concentration may emit light toward an object, and may receive light reflected from the object in 710.

The apparatus for estimating an analyte concentration may obtain a ratio of an absorption coefficient to a scattering coefficient based on the received light in 720. For example, the apparatus for estimating an analyte concentration may obtain reflectance of the object by using a quantity of the received light, and may obtain an albedo of the object using Equation 1 based on the obtained reflectance. Further, the apparatus for estimating an analyte concentration may obtain a ratio of the absorption coefficient to the scattering coefficient by using Equation 2 based on the obtained albedo.

Upon obtaining the ratio of the absorption coefficient to the scattering coefficient, the apparatus for estimating an analyte concentration may obtain a first absorption spectrum of the object from the obtained ratio of the absorption coefficient to the scattering coefficient in 730. For example, the apparatus for estimating an analyte concentration may calculate the absorbance of the object by using the absorbance calculation equation of Equation 5, and may obtain the first absorption spectrum based on the calculated absorbance.

The apparatus for estimating an analyte concentration may generate a plurality of candidate scattering correction models by varying coefficients of a function representing a change in a light path length with a wavelength in 740. For example, the apparatus for estimating an analyte concentration may generate the plurality of candidate scattering correction models by varying the coefficients E, F, and m of Equation 7.

By eliminating the scattering correction spectrum, which indicates the effect of the nonlinear change in the scattering coefficient according to a wavelength, from the first absorption spectrum by using the generated plurality of candidate scattering correction models, the apparatus for estimating an analyte concentration may obtain a plurality of second absorption spectra in 750. For example, the apparatus for estimating an analyte concentration may obtain the plurality of second absorption spectra by eliminating the effect of the scattering correction spectrum from the first absorption spectrum by using various dimension reduction algorithms, such as Principal Component Analysis (PCA), Independent Component Analysis (ICA), Non-negative Matrix Factorization (NMF), Singular Value Decomposition (SVD), and the like.

The apparatus for estimating an analyte concentration may estimate an analyte concentration for each of the second absorption spectra by using a default concentration estimation model in 760. For example, the apparatus for estimating an analyte concentration may estimate an analyte concentration for each of the second absorption spectra by using a default concentration estimation model which is represented by Equation 9.

The apparatus for estimating an analyte concentration may select, as a final scattering correction model, a candidate scattering correction model which is used for obtaining a second absorption spectrum, at which a difference between an estimated concentration and an actual concentration is minimum, from among the plurality of candidate scattering correction models in 770.

Figure 8:
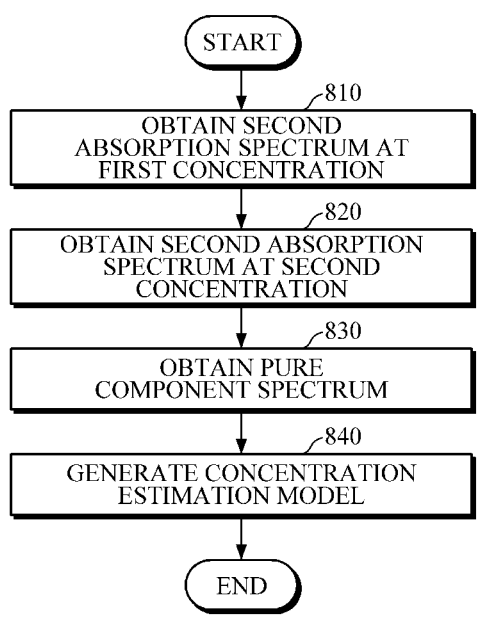
FIG. 8 is a flowchart illustrating a method of generating a concentration estimation model according to an example embodiment.

FIG. 8 is a flowchart illustrating a method of generating a concentration estimation model according to an example embodiment. The method of generating a concentration estimation model of FIG. 8 may be performed by any one of the apparatus 100 of FIG. 1 and the apparatus 600 of FIG. 6 for estimating an analyte concentration.

Referring to FIG. 8, the apparatus for estimating an analyte concentration may obtain a second absorption spectrum when the concentration of an analyte in an object is a first concentration in 810. For example, when the concentration of the analyte in the object is the first concentration, the apparatus for estimating an analyte concentration may emit light toward the object, may receive light reflected from the object, and may obtain a ratio of the absorption coefficient to the scattering coefficient based on the received light. Further, the apparatus for estimating an analyte concentration may obtain a first absorption spectrum of the object from the obtained ratio of the absorption coefficient to the scattering coefficient. In addition, based on the scattering correction model, by eliminating the effect of the scattering correction spectrum from the first absorption spectrum by using various dimension reduction algorithms, such as Principal Component Analysis (PCA), Independent Component Analysis (ICA), Non-negative Matrix Factorization (NMF), Singular Value Decomposition (SVD), and the like, the apparatus for estimating an analyte concentration may obtain the second absorption spectrum when the concentration of the analyte in the object is the first concentration.

The apparatus for estimating an analyte concentration may obtain a second absorption spectrum when the concentration of an analyte in an object is a second concentration in 820. For example, when the concentration of the analyte in the object is the second concentration, the apparatus for estimating an analyte concentration may emit light toward the object, may receive light reflected from the object, and may obtain a ratio of the absorption coefficient to the scattering coefficient based on the received light. Further, the apparatus for estimating an analyte concentration may obtain a first absorption spectrum of the object from the obtained ratio of the absorption coefficient to the scattering coefficient. In addition, based on the scattering correction model, by eliminating the effect of the scattering correction spectrum from the first absorption spectrum by using various dimension reduction algorithms, such as Principal Component Analysis (PCA), Independent Component Analysis (ICA), Non-negative Matrix Factorization (NMF), Singular Value Decomposition (SVD), and the like, the apparatus for estimating an analyte concentration may obtain the second absorption spectrum when the concentration of the analyte in the object is the second concentration.

The apparatus for estimating an analyte concentration may obtain a pure component spectrum of the analyte based on the second absorption spectrum when the concentration of the analyte in the object is the first concentration and the second absorption spectrum when the concentration of the analyte in the object is the second concentration in 830. For example, the apparatus for estimating an analyte concentration may obtain the pure component spectrum of the analyte by using Equation 10.

By using the obtained pure component spectrum of the analyte, the apparatus for estimating an analyte concentration may generate a concentration estimation model in 840. For example, the apparatus for estimating an analyte concentration may generate a concentration estimation model as represented by Equation 11.

Figure 9:
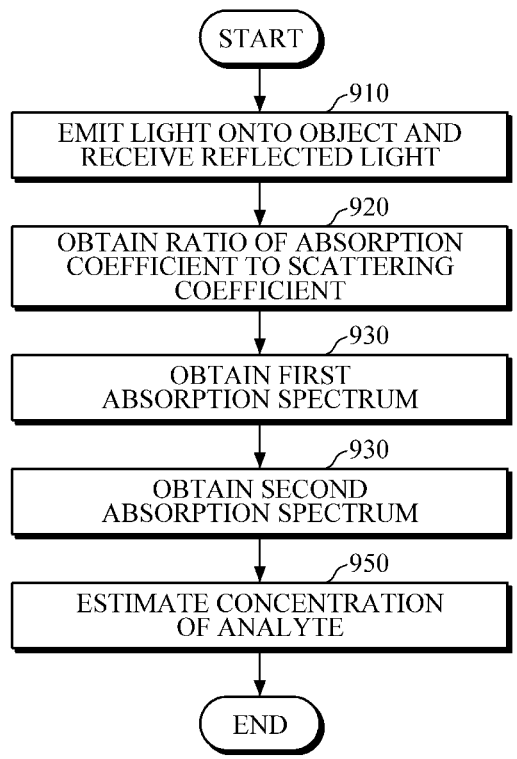
FIG. 9 is a flowchart illustrating a method of estimating a concentration of an analyte according to an example embodiment.

FIG. 9 is a flowchart illustrating a method of estimating a concentration of an analyte. The method of estimating an analyte concentration of FIG. 9 may be performed by any one of the apparatus 100 and the apparatus 600 for estimating an analyte concentration of FIG. 1 or FIG. 6.

The apparatus for estimating an analyte concentration may emit light toward an object, and may receive light reflected from the object in 910.

The apparatus for estimating an analyte concentration may obtain a ratio of the absorption coefficient to the scattering coefficient based on the received light in 920. For example, the apparatus for estimating an analyte concentration may obtain reflectance of the object by using a quantity of the received light, and may obtain an albedo of the object by using Equation 1 based on the obtained reflectance. Further, the apparatus for estimating an analyte concentration may obtain a ratio of the absorption coefficient to the scattering coefficient by using Equation 2 based on the obtained albedo.

Upon obtaining the ratio of the absorption coefficient to the scattering coefficient, the apparatus for estimating an analyte concentration may obtain a first absorption spectrum of the object from the obtained ratio of the absorption coefficient to the scattering coefficient in 930. For example, the apparatus for estimating an analyte concentration may obtain the first absorption spectrum by using the absorbance calculation equation of Equation 5, which is expressed as a function of the ratio of the absorption coefficient to the scattering coefficient.

By eliminating the scattering correction spectrum, which indicates the effect of the nonlinear change in the scattering coefficient according to a wavelength, from the first absorption spectrum by using the scattering correction model, the apparatus for estimating an analyte concentration may obtain the second absorption spectrum in 940. For example, by using various dimension reduction algorithms, such as Principal Component Analysis (PCA), Independent Component Analysis (ICA), Non-negative Matrix Factorization (NMF), Singular Value Decomposition (SVD), and the like based on the scattering correction model as represented by Equation 8, the apparatus for estimating an analyte concentration may obtain the second absorption spectrum from the first absorption spectrum.

Upon obtaining the second absorption spectrum, the apparatus for estimating an analyte concentration may estimate the analyte concentration by using the second absorption spectrum and the concentration estimation model in 950. In this case, the apparatus for estimating an analyte concentration according to an example embodiment may estimate the analyte concentration by using various dimension reduction algorithms, such as Principal Component Analysis (PCA), Independent Component Analysis (ICA), Non-negative Matrix Factorization (NMF), Singular Value Decomposition (SVD), and the like. The concentration estimation model may be represented by Equation 9 or Equation 11.

Figure 10:
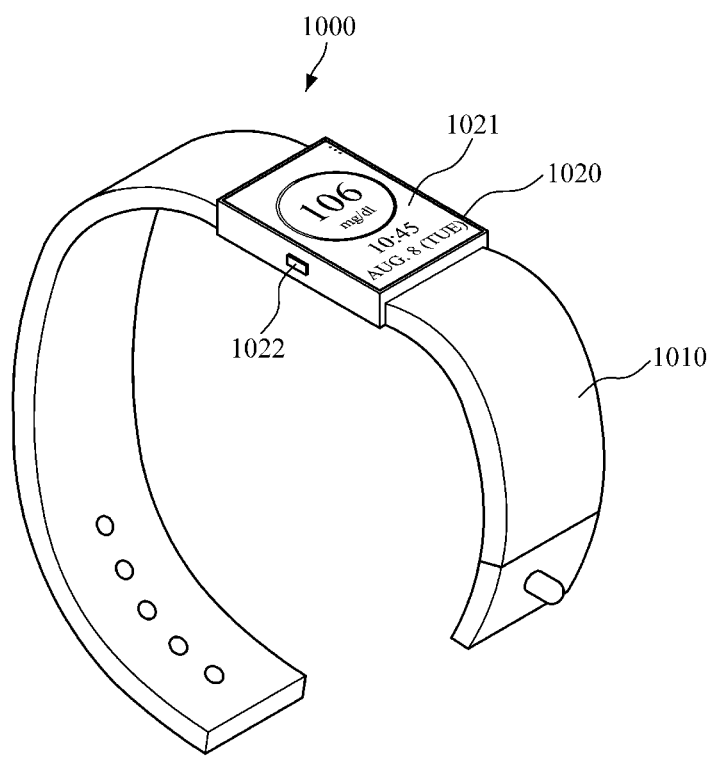
FIG. 10 is a diagram illustrating a wrist-type wearable device according to an example embodiment.

FIG. 10 is a diagram illustrating a wrist-type wearable device according to an example embodiment.

Referring to FIG. 10, the wrist-type wearable device 1000 includes a strap 1010 and a main body 1020.

The strap 1010 may be connected to both ends of the main body 1020 so as to be fastened in a detachable manner or may be integrally formed therewith as a smart band. The strap 1010 may be made of a flexible material to be wrapped around a user's wrist so that the main body 1020 may be worn on the wrist.

The main body 1020 may include any one of the aforementioned apparatuses 100 and 600 for estimating an analyte concentration. Further, the main body 1020 may include a battery which supplies power to the wrist-type wearable device 1000 and any one of the apparatuses 100 and 600 for estimating an analyte concentration.

A biometric sensor may be mounted at the main body 1020 (e.g., at a rear surface of the main body 1020) to be exposed to a user's wrist. Accordingly, when a user wears the wrist-type wearable device 1000, the biometric sensor may naturally come into contact with the user's skin.

The wrist-type wearable device 1000 may further include a display 1021 and an input interface 1022 which are mounted on the main body 1020. The display 1021 may display data processed by the wrist-type wearable device 1000 and any one of the apparatuses 100 and 600 for estimating an analyte concentration, processing result data thereof, and the like. The input interface 1022 may receive various operation signals from a user.

The disclosure can be implemented as a computer-readable code written on a computer-readable recording medium. Codes and code segments needed for implementing the disclosure can be easily deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

Example embodiments have been described. However, it will be apparent to those skilled in the art that various changes and modifications can be made without departing from the inventive concept of the disclosure. Thus, it should be understood that the above-described example embodiments are not intended to limit the disclosure, but include various modifications and equivalents included within the spirit and scope of the appended claims.

What is claimed is:

1. An apparatus for estimating a concentration of an analyte, the apparatus comprising:
   an optical sensor configured to emit light toward an object and receive light reflected from the object; and
   a processor configured to:
   obtain a ratio of an absorption coefficient to a scattering coefficient based on the received light,
   obtain a first absorption spectrum of the object based on the obtained ratio,
   obtain a second absorption spectrum by eliminating a scattering correction spectrum from the first absorption spectrum, the scattering correction spectrum corresponding to a nonlinear change in the scattering coefficient according to a wavelength of the emitted light, and
   estimate a concentration of an analyte based on the second absorption spectrum,
   wherein the scattering correction spectrum is expressed as a function representing a change in a length of a light path according to the wavelength of the emitted light, and
   wherein the processor is further configured to obtain the second absorption spectrum by using a scattering correction model that is based on the function.

2. The apparatus of claim 1, wherein the processor is further configured to:
   obtain a reflectance of the object based on the received light,
   obtain an albedo of the object based on the obtained reflectance, and
   obtain the ratio of the absorption coefficient to the scattering coefficient based on the obtained albedo.

3. The apparatus of claim 1, wherein the processor is further configured to obtain the first absorption spectrum based on a function of the ratio of the absorption coefficient to the scattering coefficient.

4. The apparatus of claim 1, wherein the processor is further configured to:
   generate a plurality of candidate scattering correction models by varying coefficients of the function,
   obtain a plurality of second absorption spectra by using the first absorption spectrum and the plurality of candidate scattering correction models,
   estimate a concentration of the analyte for each of the plurality of second absorption spectra, and
   select, as the scattering correction model, a candidate scattering correction model, in which a difference between an estimated concentration and an actual concentration of the analyte is minimum, from among the plurality of candidate scattering correction models.

5. The apparatus of claim 1, wherein the processor is further configured to estimate the concentration of the analyte by using the second absorption spectrum and a pure component spectrum of the analyte.

6. The apparatus of claim 5, wherein the pure component spectrum of the analyte is set as a default or is obtained and set in a calibration mode.

7. The apparatus of claim 6, wherein in the calibration mode, the processor is further configured to obtain the pure component spectrum based on a difference between the second absorption spectrum, obtained when the concentration of the analyte in the object is a first concentration, and the second absorption spectrum obtained when the concentration of the analyte in the object is a second concentration.

8. The apparatus of claim 1, wherein the processor is further configured to obtain the second absorption spectrum by eliminating the scattering correction spectrum from the first absorption spectrum by using one of Principal Component Analysis (PCA), Independent Component Analysis (ICA), Non-negative Matrix Factorization (NMF), and Singular Value Decomposition (SVD).

9. The apparatus of claim 1, wherein the analyte comprises at least one of glucose, triglyceride, urea, uric acid, lactate, protein, cholesterol, antioxidant substance, and ethanol.

10. A method of estimating a concentration of an analyte, the method comprising:
    emitting light toward an object and receiving light reflected from the object;
    obtaining a ratio of an absorption coefficient to a scattering coefficient based on the received light;
    obtaining a first absorption spectrum of the object from the obtained ratio of the absorption coefficient to the scattering coefficient;
    obtaining a second absorption spectrum by eliminating a scattering correction spectrum from the first absorption spectrum, the scattering correction spectrum corresponding to a nonlinear change in the scattering coefficient according to a wavelength of the emitted light; and
    estimating a concentration of an analyte based on the second absorption spectrum,
    wherein the scattering correction spectrum is expressed as a function representing a change in a length of a light path according to the wavelength of the emitted light; and
    wherein the obtaining the second absorption spectrum comprises obtaining the second absorption spectrum by using a scattering correction model based on the function.

11. The method of claim 10, wherein the obtaining the ratio comprises:
    obtaining reflectance of the object based on the received light;
    obtaining an albedo of the object based on the obtained reflectance; and
    obtaining the ratio of the absorption coefficient to the scattering coefficient based on the obtained albedo.

12. The method of claim 10, wherein the obtaining the first absorption spectrum comprises obtaining the first absorption spectrum based on a function of the ratio of the absorption coefficient to the scattering coefficient.

13. The method of claim 10, wherein the estimating comprises estimating the concentration of the analyte by using the second absorption spectrum and a pure component spectrum of the analyte.

14. The method of claim 13, wherein the pure component spectrum of the analyte is set as a default or is obtained and set in a calibration mode.

15. The method of claim 10, wherein the obtaining the second absorption spectrum comprises obtaining the second absorption spectrum by eliminating the scattering correction spectrum from the first absorption spectrum by using one of Principal Component Analysis (PCA), Independent Component Analysis (ICA), Non-negative Matrix Factorization (NMF), and Singular Value Decomposition (SVD).

16. The method of claim 10, wherein the analyte comprises at least one of glucose, triglyceride, urea, uric acid, lactate, protein, cholesterol, antioxidant substance, and ethanol.

17. A method of calibrating an apparatus for estimating a concentration of an analyte, the method comprising:
emitting light toward an object and receiving light reflected from the object;
obtaining a ratio of an absorption coefficient to a scattering coefficient based on the received light;
obtaining a first absorption spectrum of the object from the obtained ratio of the absorption coefficient to the scattering coefficient;
generating a plurality of candidate scattering correction models by varying coefficients of a function representing a change in a length of a light path according to a wavelength of the emitted light;
obtaining a plurality of second absorption spectra by using the first absorption spectrum and the plurality of candidate scattering correction models;
estimating a concentration of an analyte for each of the plurality of second absorption spectra; and
selecting a candidate scattering correction model, in which a difference between an estimated concentration and an actual concentration of the analyte is minimum, from among the plurality of candidate scattering correction models.

18. The method of claim 17, wherein the obtaining the ratio comprises:
obtaining reflectance of the object based on the received light;
obtaining an albedo of the object based on the obtained reflectance; and
obtaining the ratio of the absorption coefficient to the scattering coefficient based on the obtained albedo.

19. The method of claim 17, wherein the obtaining the first absorption spectrum comprises obtaining the first absorption spectrum based on a function of the ratio of the absorption coefficient to the scattering coefficient.

20. The method of claim 17, wherein the estimating comprises estimating the concentration of the analyte for each of the plurality of second absorption spectra by using each of the plurality of second absorption spectra and a pure component spectrum of the analyte.

21. The method of claim 17, wherein the obtaining the plurality of second absorption spectra comprises obtaining the plurality of second absorption spectra by using one of Principal Component Analysis (PCA), Independent Component Analysis (ICA), Non-negative Matrix Factorization (NMF), and Singular Value Decomposition (SVD).

22. The method of claim 17, wherein the analyte comprises at least one of glucose, triglyceride, urea, uric acid, lactate, protein, cholesterol, antioxidant substance, and ethanol.

23. A method of calibrating an apparatus for estimating a concentration of an analyte, the method comprising:
emitting first light toward an object and receiving second light reflected from the object, a concentration of an analyte in the object being a first concentration;
obtaining a first ratio of an absorption coefficient to a scattering coefficient based on the received second light;
obtaining a first absorption spectrum of the object from the obtained first ratio;
obtaining a second absorption spectrum by eliminating a first scattering correction spectrum from the first absorption spectrum, the first scattering correction spectrum corresponding to a nonlinear change in the scattering coefficient according to a wavelength of the emitted first light;
emitting third light toward the object and receiving fourth light reflected from the object, the concentration of the analyte in the object being a second concentration;
obtaining a second ratio of the absorption coefficient to the scattering coefficient based on the received fourth light;
obtaining a third absorption spectrum of the object from the obtained second ratio;
obtaining a fourth absorption spectrum of the analyte by eliminating a second scattering correction spectrum from the third absorption spectrum, the second scattering correction spectrum corresponding to the nonlinear change in the scattering coefficient according to a wavelength of the emitted third light; and
obtaining a pure component spectrum of the analyte based on the obtained second absorption spectrum and the obtained fourth absorption spectrum,
wherein the first scattering correction spectrum is expressed as a first function representing a change in a length of a light path according to the wavelength of the emitted first light; and
wherein the obtaining the second absorption spectrum comprises obtaining the second absorption spectrum by using a scattering correction model based on the function.

24. The method of claim 23, wherein the obtaining the pure component spectrum comprises obtaining the pure component spectrum by using a difference between the fourth absorption spectrum and the second absorption spectrum, and a difference between the second concentration and the first concentration.

25. The method of claim 23, further comprising generating a concentration estimation model by using the obtained pure component spectrum.

* * * * *